United States Patent
Tomaru

(10) Patent No.: US 7,700,932 B2
(45) Date of Patent: Apr. 20, 2010

(54) METHOD, SET, AND APPARATUS FOR OBTAINING PRINTS OF A PART OF THE HUMAN BODY

(75) Inventor: Yuichi Tomaru, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/191,328

(22) Filed: Aug. 14, 2008

(65) Prior Publication Data
US 2008/0305240 A1 Dec. 11, 2008

Related U.S. Application Data

(62) Division of application No. 11/036,211, filed on Jan. 18, 2005, now Pat. No. 7,442,401.

(30) Foreign Application Priority Data

Jan. 15, 2004 (JP) .............................. 2004-007874

(51) Int. Cl.
*G06K 5/00* (2006.01)
*A61B 5/103* (2006.01)

(52) U.S. Cl. .......................................... 250/556; 427/1
(58) Field of Classification Search ................. 250/556; 382/124, 125; 427/1
See application file for complete search history.

(56) References Cited

U.S. PATENT DOCUMENTS

| | | | | |
|---|---|---|---|---|
| 5,079,029 A | * | 1/1992 | Saunders | ......................... 427/1 |
| 6,180,415 B1 | * | 1/2001 | Schultz et al. | .............. 436/518 |
| 6,476,409 B2 | | 11/2002 | Iwasaki et al. | |
| 6,784,007 B2 | | 8/2004 | Iwasaki et al. | |
| 7,079,250 B2 | | 7/2006 | Mukai | |
| 2003/0179323 A1 | * | 9/2003 | Abileah et al. | ................. 349/24 |

FOREIGN PATENT DOCUMENTS

| | | |
|---|---|---|
| JP | 2001-009800 A | 1/2001 |
| JP | 2003-232725 A | 8/2003 |
| JP | 2003-268592 A | 9/2003 |

* cited by examiner

*Primary Examiner*—Thanh X Luu
(74) *Attorney, Agent, or Firm*—Sughrue Mion, PLLC

(57) ABSTRACT

A part of a human body is caused to contact the surface layer of a recording medium over which a plurality of metallic grains with an outside size of 200 nm or less are distributed. Then, secretions from the skin surface of the body part are caused to adhere to the surface layer of the recording medium to take the print of the body part. If light is irradiated to the recording medium, specific optical characteristics resulting from the surface structure of the recording medium are obtained, and therefore the color of the recording medium varies between a region having secretions and a region having no secretions. This renders it possible to record a visible print on the recording medium.

3 Claims, 2 Drawing Sheets

METHOD, SET, AND APPARATUS FOR OBTAINING PRINTS OF A PART OF THE HUMAN BODY

This is a divisional of application Ser. No. 11/036,211 filed Jan. 18, 2005. The entire disclosure of the prior application, application Ser. No. 11/036,211 is hereby incorporated by reference.

BACKGROUND OF THE INVENTION

1. Field of the Invention

The present invention relates to a method of obtaining prints of the shape or patterns of a part of the human body, such as a handprint, a footprint, a fingerprint, etc., and to a set and apparatus for obtaining such prints by the method.

2. Description of the Related Art

Human handprints and footprints are taken as a record of a child's growth or as a proof of a celebrity's visit and they are left in commemoration. Also, fingerprints are sometimes employed to identify a person. The print of a hand or a foot is usually taken by applying ink or India ink to the hand or foot and then impressing it on colored paper. Recently, a handprint or footprint impressed on paper has been read by a scanner and stored or reproduced as digital data (see Japanese Unexamined Patent Publication No. 2002-314795). In the case of the fingerprints, the digital data is sometimes utilized to check fingerprints.

However, in the aforementioned conventional method, it is necessary to wash ink or India ink left on a hand or foot after the print of the hand or foot is taken, so it is difficult to take the print of a part of the human body in an environment having no washing facilities. In addition, there is a possibility that when taking such a print, clothes will be stained with ink or India ink, so suitable preparation is needed beforehand.

Furthermore, the number of persons having sensitive skin or allergies is increasing, so that there is apprehension about the influence of chemicals contained in ink on the skin. Particularly, when taking infant handprints or footprints, ink for obtaining prints of a hand or foot requires high safety.

SUMMARY OF THE INVENTION

The present invention has been made in view of the circumstances mentioned above. Accordingly, it is an object of the present invention to provide a method that makes it easy to obtain a handprint, a footprint, a fingerprint, etc., without being limited to time, location, or physical constitution. Another object of the invention is to provide a set and apparatus for taking such a print by the method.

The method of the present invention is a method of obtaining prints of the shape or patterns of at least a part of a human body. The print of the shape refers to a print representing the contours of a human body. Examples are a handprint, a footprint, etc. The print of the patterns means a print that represents irregularities on the skin surface of a human body. Examples are fingerprints, lines in the palm of a hand, etc.

The method of the present invention utilizes specific optical characteristics resulting from the surface structure of a recording medium to take the print of a part of a human body. More specifically, in accordance with the present invention, there is provided a method of obtaining prints of the shape and/or patterns of at least a part of a human body. The method comprises a step of causing the aforementioned part to contact a surface layer of a recording medium, over which a plurality of metallic grains with an outside size of 200 nm or less are distributed, and a step of causing secretions from a skin surface of the aforementioned part to adhere to the surface layer of the recording medium to take the aforementioned print. In a recording medium that has the aforementioned surface structure, the reflection characteristics of light at a region having secretions changes considerably. For this reason, if only secretions are caused to adhere to the recording medium, a print visible to the eyes of an observer can be recorded.

The aforementioned outside size refers to the size of the largest part of the metallic grain. For instance, if the metallic grain is a sphere or an ellipsoid, the outside size refers to the diameter. Also, if the metallic grain is a rectangular parallelepiped, the outside size refers to the height or width.

In the method of the present invention, the surface layer of the recording medium is preferably a layer in which the metallic grains are provided in alumina minute holes obtained by anodizing a material that contains aluminum as its main component. The minute holes, naturally formed when aluminum or an aluminum alloy is anodized, are arranged with high regularity. Therefore, if metallic grains are provided in the minute holes, the metallic grains are also arranged with high regularity.

In the method of the present invention, the surface layer is preferably coated with a layer having a refractive index different from that of secretions, after the secretions adhere to the surface layer of the recording medium. In this case, since the secretions are isolated from air, it is prevented from decomposing or being wiped off. Thus, long-term storage of the recording medium becomes possible.

In addition, a print taken by the aforementioned method may be stored as digital image, by optically reading the recording medium after the secretion adheres to the surface layer of the recording medium, then generating a digital image representing an adhesion status of the secretion, and storing the digital image on a predetermined storage medium.

In accordance with the present invention, there is provided a print taking set. The set comprises a recording medium in which a plurality of metallic grains with an outside size of 200 nm or less are distributed over a surface layer, and a coating member. The coating member can be applied to or stuck on the surface layer of the recording medium, and comprises a material that has a refractive index different from any refractive index of secretions from a human skin. The material of the coating member doesn't matter if it can fix secretions adhering to the recording medium so that the secretions are isolated from air. It is preferably a sheet member, but may be a coating fluid that hardens when dried.

In accordance with the present invention, there is provided a print taking apparatus. The apparatus comprises a recording medium image generation means, and data storage means. In the recording medium, a plurality of metallic grains with an outside size of 200 nm or less are distributed over the surface layer. The image generation means is used for optically reading out the recording medium and generating a digital image representing an adhesion status of a substance to the recording medium. The data storage means is used for storing the generated digital image on a predetermined data storage medium.

The print taking method of the present invention does not require ink or India ink, because the print of a hand or a foot is recorded on a recording medium by making use of specific optical characteristics resulting from the surface structure of the recording medium. For this reason, handprints, footprints, etc., can be easily taken regardless of the presence or absence of washing facilities, clothes, and physical constitution. In addition, the recording medium can be reused if secretions are removed therefrom, and consequently, prints can be easily retaken.

The print taking set of the present invention comprises the aforementioned recording medium and a member for coating the recording medium. Since the recording medium can be coated immediately after a print is taken, the taken print can be stored in an optimal state.

The print taking apparatus of the present invention optically reads a print taken by the aforementioned method and stores the print as a digital image. Thus, the recording medium can be reused if secretions are removed therefrom. The taken print can also be processed or reproduced as a digital image.

BRIEF DESCRIPTION OF THE DRAWINGS

The present invention will be described in further detail with reference to the accompanying drawings wherein.

DESCRIPTION OF THE PREFERRED EMBODIMENTS

Figure 1:
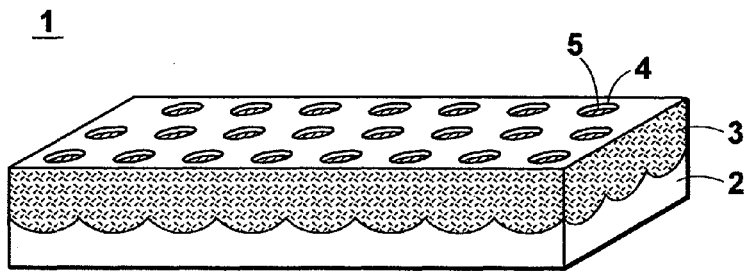
FIG. 1 is a perspective view showing a recoding medium fabricated in accordance with a first embodiment of the present invention.

Referring now in greater detail to the drawings and initially to FIG. 1, there is shown a recording medium 1 fabricated in accordance with a first embodiment of the present invention. As shown in the figure, the recording medium 1 comprises an aluminum substrate 2, an alumina layer 3 obtained by anodizing the aluminum substrate 2, and gold grains 5 held in minute holes 4 formed in the surface of the alumina layer 3. The recording medium 1 can be formed into an arbitrary size, depending on the type of print that is to be taken. Only part of the recording medium 1 is shown in FIG. 1.

Figure 2:
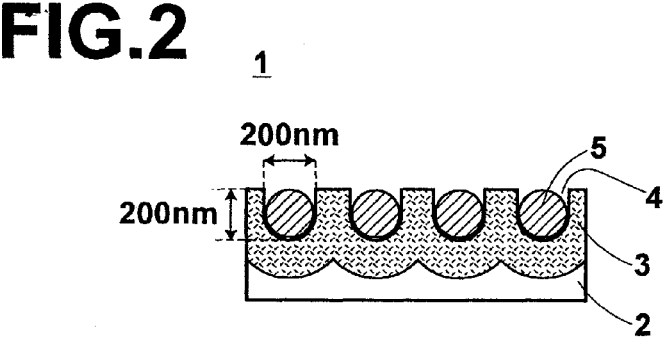
FIG. 2 is a sectional view of the layer structure of the recording medium shown in FIG. 1.

FIG. 2 shows a sectional view of the layer structure shown in FIG. 1. In this embodiment, the minute hole 4 is 200 nm in depth and diameter and the grain diameter of the gold grain 5 in the minute hole 4 is smaller than 200 nm. The minute holes 4 are disposed at intervals of about 200 nm.

The alumina layer 3 is a porous oxide coating and is formed by anodizing the aluminum substrate 2 in a suitable acid electrolyte. To anodize the surface of the aluminum substrate 2, the aluminum substrate 2 is fixed to the holder of anodizer and is immersed in an electrolyte within a reaction container along the opposite electrode. The electrolyte is, for example, oxalic acid, phosphoric acid, sulfuric acid, or chromic acid solution. The electrolyte may be a mixture of acid solutions of two or more kinds.

Next, a voltage is applied between the aluminum substrate 2 and the opposite electrode. At this time, the aluminum substrate 2 is connected to the plus side of a power source, while the opposite electrode is connected to the minus side. When the voltage is applied, first, the aluminum substrate 2 is coated with an oxide layer, and then minute holes are formed in the oxide layer by the dissolution action of the aforementioned acid solution.

Some of the minute holes 4 grow preferentially with the progress of anodic oxidation and are arranged at approximately equal spaces. Since an electric field applied to portions where holes are formed is higher than that of other portions, dissolution is accelerated at the holed portions and therefore the holes grow in the direction perpendicular to the surface of the aluminum substrate 2. On the other hand, portions around the holes 4 are left on the surface of the alumina layer 3 without being dissolved.

The hole diameter, depth, and interval vary depending on anodic oxidation conditions (e.g., the concentration and temperature of an electrolyte employed in anodic oxidation, voltage-application method, voltage value, time, etc.). The minute holes 4 can be accurately controlled in a range where the interval between minute holes 4 is 10 to 500 nm and the hole diameter is 5 to 400 nm. Therefore, if suitable conditions are set, the layer structure shown in FIG. 2 is obtainable.

The minute holes 4 in the alumina layer 3 are arranged with great regularity, so if the gold grains 5 are respectively arranged in the minute holes, regular arrangement of the gold grains 5 can be obtained.

To arrange the gold grains 5 in the minute holes 4, gold is first deposited on the surface in which the minute holes 4 are formed. Then, the gold deposited on around the minute holes 4 is removed so that each minute hole 4 is filled with the gold grain 5. Instead of deposition, each minute hole 4 may be filled with the gold grain 5 by electroplating.

Now, a description will be given of how a print is taken by the recording medium 1 described above. As an example, a handprint will be taken as follows.

To take a handprint, a recording medium with a surface area larger than a hand is first prepared. The hand is then impressed on the surface of the recording medium 1, that is, the surface in which the gold grains 5 are arranged.

Figure 3:
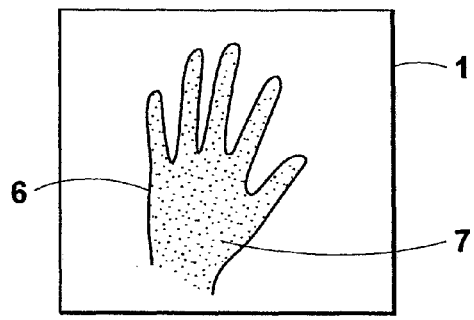
FIG. 3 is a plan view showing the recording medium, to which secretions adhere.

At this time, the hand is preferably in a wet state in which sweat or sebum is secreted, not in a dry state. If the hand is dry, sebum or sweat from other parts of the body or saliva is applied to the hand in advance. If the hand in the wet state is impressed on the surface of the recording medium 1, secretions 7 such as sebum will adhere to a hand-impressed region 6, as shown in FIG. 3.

The present inventors have found that when a print is taken in the above-described steps with the recording medium 1, clearer contrast is obtained compared with the case where the sebum of a hand is caused to adhere to another medium (e.g., glass). It is considered that the reason why clearer contrast than that of other mediums is obtained is due to the following reason. That is, the reason is that the wavelength and intensity of light reflected at the surface of the recording medium 1 change considerably, depending on specific optical characteristics resulting from the surface structure of the recording medium 1.

As the specific optical characteristics, there is a local plasmon resonance phenomenon by way of example. The local plasmon resonance phenomenon is a phenomenon where, when light is irradiated to a metallic grain smaller than the wavelength of the light, free electrons within the metallic grain start to vibrate in resonance with the electric field of the light. If free electrons start to vibrate, that is, if local plasmon resonance is induced, a strong electric field occurs around a metallic grain and scattering and absorption increase at a specific wavelength (hereinafter referred to as a resonance wavelength). Since the resonance wavelength depends on the refractive index of a substance around a metallic grain, a reflection characteristic varies between the case where there is some substance around the periphery and the case where there is no substance around the periphery. If the refractive index of a peripheral substance becomes greater, the resonance wavelength will be shifted to a long wavelength side and light scattering and absorption will increase.

Figure 4:
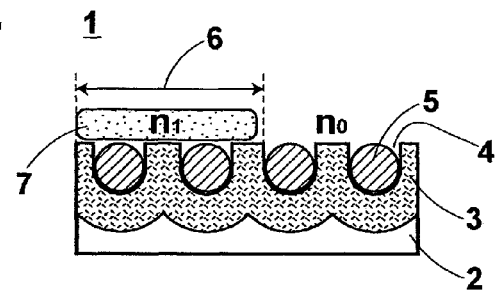
FIG. 4 is a sectional view of the recording medium shown in FIG. 3.

FIG. 4 shows a sectional view of the boundary between the hand-impressed region 6 and a hand-unimpressed region. As shown in the figure, in the hand-impressed region 6, the secretion 7 such as sebum adheres to the surface of the recording medium 1. For this reason, the refractive index n1 of the secretion 7 on the gold grains 5 is greater than the refractive index n0 of air. When the refractive index n0 of air is 1, the refractive index n1 of the secretion 7 is about 1.45 to 1.47.

Figure 5:
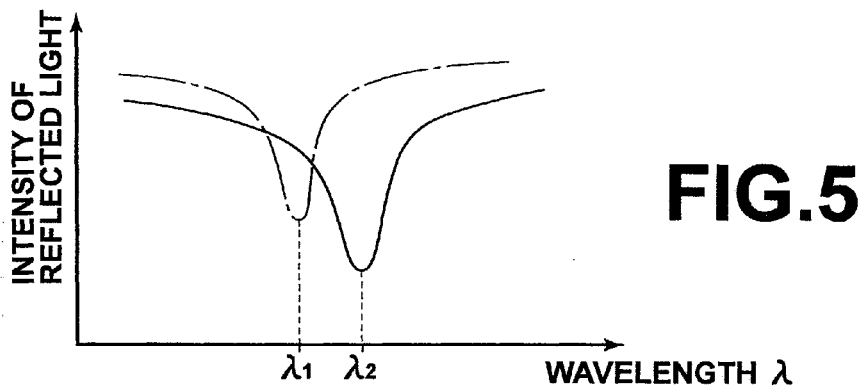
FIG. 5 is a graph showing the intensity of reflected light due to a local plasmon resonance phenomenon.

FIG. 5 shows the intensity of reflected light obtained when light is irradiated onto the gold grains 5. The horizontal axis represents the wavelength of light, while the vertical axis represents the intensity of reflected light. In FIG. 5, a broken line indicates the reflection characteristic obtained at an unimpressed region where there are no secretions, and a full line indicates the reflection characteristic obtained at an impressed region where there are secretions. As shown in the figure, the resonance wavelength $\lambda 1$ at an unimpressed region with no secretion differs from the resonance wavelength $\lambda 2$ at an impressed region with secretions. When the secretions are sweat or sebum, the difference between $\lambda 1$ and $\lambda 2$ is 150 nm or so. The intensity of light reflected at an impressed region is smaller than that at an unimpressed region.

In practice, the hand of a person has bulging parts and depressed parts, so secretions do not always adhere to a recording medium uniformly. Therefore, there are parts where secretions adhere thickly and parts where secretions hardly adhere. The intensity of reflected light varies with the thickness of the secretions. If the secretions adhere thicker, the intensity of reflected light at the thicker part becomes smaller.

If the wavelength of absorbed light varies between an impressed region to which secretions adhere and an unimpressed region to which no secretion adheres, the colors of the impressed region and unimpressed region are visibly different to the naked eye. As previously mentioned, the resonance wavelength varies 150 nm between an impressed region to which secretions adhere and an unimpressed region to which no secretion adheres, so a clear change in color can be observed. Also, if the intensity of reflected light varies between a thick region to which secretions adhere thickly and a thin region to which secretions adhere thinly, the irregularities on a skin surface can be discriminated as shades of color on the recording medium 1.

Thus, if only secretions from the skin surface of a human hand is caused to adhere to the recording medium 1, a clear print with relatively great contrast can be obtained. It is considered that the reason is due to the surface structure of the recording medium 1 which can easily induce a local plasmon resonance phenomenon.

Particularly, when the size of the metal grain is 200 nm or less, a clear print is obtainable. The present invention is not limited to the recording medium 1 shown in FIG. 2. If the sweat or sebum of a human hand is caused to adhere to a recording medium where a plurality of gold grains of the aforementioned size are distributed over the entire surface of the surface layer, a clear print can be similarly obtained.

Figure 6:
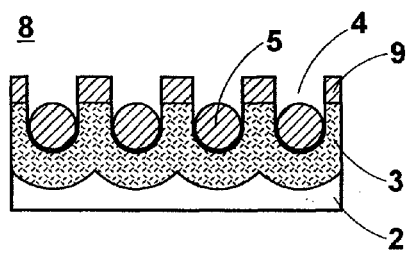
FIG. 6 is a sectional view showing a recoding medium fabricated in accordance with a second embodiment of the present invention.

As shown in FIG. 6, a gold thin film 9 may be formed on a portion of a recording medium surface other than that in which the minute holes 4 are formed. The gold thin film 9 can be formed by depositing gold. At this time, the distance between the gold thin film 9 and the gold grain 5 is preferably less than the grain diameter of the gold grain 5. That is, the distance between the top end of the gold grain 5 and the bottom end of the gold thin film 9 is less than the grain diameter of the gold grain 5. When forming minute holes 4 by anodizing the aluminum substrate 2, the depth of the minute holes 4 can be freely adjusted by controlling the conditions of anodic oxidation. Therefore, at the stage of anodic oxidation, if the depth of the minute holes 4 is set so that the distance between the gold thin film 9 and the gold grain 5 is less than the grain diameter of the gold grain 5, the recording medium 8 shown in FIG. 6 can be fabricated.

In the layer structure shown in FIG. 6, near-field light produced when light is irradiated to the gold grains 5 interacts with the gold thin film 9, so that an absorption spectrum due to an electric multipole occurs. With the synergistic effect between local plasmon resonance and the electric multipole, a change in reflected light becomes sharper with respect to a change in the refractive index of a medium around gold grains. Therefore, it is contemplated that a clearer print can be taken with the recording medium.

Also, in the case of a recording medium where a plurality of metallic grains are distributed over the entire surface of the surface layer, the occurrence of a local plasmon phenomenon is not limited to the case where the metallic grains are gold. Therefore, the metal in the minute hole or metal deposited on the surface may be silver (Ag), copper (Cu), or aluminum (Al). Even in cases other than those in which gold is employed, a recognizable print can be likewise taken. Gold is suitable for long-term storage, because deposition can be performed at a relatively low temperature and therefore a recording medium is easy to fabricate, and because it is corrosion-resistant. Silver is easily oxidizable, but is superior in contrast to gold. Also, since copper and aluminum are cheaper than gold and silver, fabrication costs for a recording medium can be reduced. Thus, metals have respective characteristics. Therefore, the material of metallic grains is preferably selected according to purposes.

In the embodiments shown in FIGS. 1 to 6, regular arrangement of metal grains is formed by filling minute holes with metal in an anodic oxidation process, but the recording medium used in taking a print can be fabricated by other methods. For instance, minute holes may be formed in a substrate and filled with metal by semiconductor fabrication techniques such as electro-beam lithography. In addition, although there is a disadvantage that grains are easy to cohere, a recording medium can be fabricated by a method of immersing the recording medium surface in a metal colloid solution and fixing metal grains in the surface.

That is, the recording medium employed in the print taking method of the present invention may be fabricated by any method, as long as metal grains with an outside size of 200 nm or less are distributed over the entire surface of the surface layer. However, it is most preferable, from the viewpoint of the quality of a print, to fabricate a recording medium by a method that arranges metal grains regularly, by making use of the regularity of alumina minute holes formed by anodic oxidation.

In the recording medium employed in the print taking method of the present invention, the configuration of the recording medium main body is not particularly limited as long as the surface layer is constructed as described above. While the recording media shown in FIGS. 1 and 6 are of a sheet type, they may be a spherical type where metal grains are arranged in the surface of a sphere, or a box type where metal grains are arranged in each surface of a box.

In a recording medium having secretions such as sebum, it is considered that a change in the absorption wavelength and intensity of reflected light is mainly caused by light interference and a local plasmon phenomenon. The reason is that when light beams, reflected in two or more directions due to the influence of secretions on the surface of a recording medium, interfere with each other and light with a specific wavelength is cancelled, a change in color is observed by the naked eye. The present inventors have contemplated that if the surface structure of a recording medium is determined so that the wavelength cancelled due to interference and the wavelength due to a local plasmon resonance are aligned or superposed, contrast can be further enhanced compared with the case where one of the two phenomena is utilized.

Now, a description will be given of how a print is stored. There is a possibility that secretions adhering to a recording medium will decompose with the lapse of time or will be wiped off by contact with an object. For this reason, it is preferable that the surface of the recording medium be coated after a print is taken. For example, the recording medium may be covered with a coating sheet, or the recording medium surface may be coated with a layer by applying a coating fluid and drying.

A coating member is a member that can prevent secretions, which are adhered to the recording medium from being decomposed and wiped off and has a refractive index different from that of the secretion. However, if a coating member meets these conditions, the material of the coating member is not particularly limited.

More specifically, a transparent plastic film can be employed as a coating member. Examples of transparent plastic films meeting the above-described conditions are a transparent film of polyethylene terephthalate (refractive index 1.65) and a transparent film of polycarbonate (refractive index 1.55). In addition, the coating member may be optical glass. Examples of optical glasses meeting the above-described conditions are SF-13 (refractive index 1.73 to 1.75) and BaK4 (refractive index 1.56 to 1.57).

By providing a coating, transportation and storage of a recording medium having a print are facilitated. Particularly, when a transparent plastic film is used as a coating member, a recording medium is light in weight and easy to handle.

As another method of storing a print, there is a method of optically reading a recording medium having a print and then generating a digital image representing an adhesion status of the secretion. For instance, reading of a print is performed by irradiating light to a recording medium after the print is taken. Then, digital data is acquired for each pixel by converting the reflected light into an electrical signal with a charge coupled device (CCD), to generate image data. Note that a print taken on a recording medium by the aforementioned method has a plurality of colors, unlike a conventional print taken with ink, etc. Therefore, when storing the print as image data, it is desirable to store it as a color image.

Figure 7:
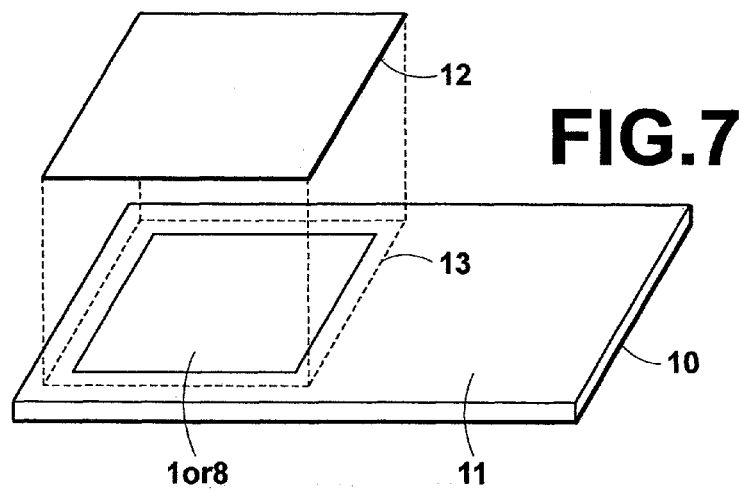
FIG. 7 is a perspective view of a print taking set of the present invention that employs the recording medium shown in FIG. 1.

Referring now to FIG. 7, there is shown a print taking set according to the present invention. As shown in the figure, the print taking set is composed of a print taking sheet 10 and a coating sheet 12. The print taking sheet 10 is constructed of a colored paper sheet or plastic sheet member on which the recording medium 1 having the layer structure shown in FIG. 2 (recording medium 8 having the layer structure shown in FIG. 6) is stuck. The size of the recording medium is smaller than the print taking sheet 10, and the date the print was taken, a signature, etc., can be recorded on a blank region 11 of the print taking sheet 10.

The coating sheet 12 is used to protect a print taken on the recording medium and is constructed of a coating member such as the aforementioned coating member. After a print is taken by impressing a human hand on the recording medium 1, the coating sheet 12 is stuck on a region 13 indicated by a broken line so as to cover the recording medium 1. In this manner, secretions on the recording medium 1 are covered with the coating sheet 12, so the print taken on the recording medium 1 can be satisfactorily stored. Note that the coating sheet 12 may have an end stuck on the print taking sheet 10 in advance. In this cast, the entirety of the coating sheet 12 is stuck on the recording medium 1 after a print is taken.

The print taking set of the present invention is easy to carry and does not require any special tools when taking a print. In addition, since the print is immediately coated, it can be stored in an optimal state.

Figure 8:
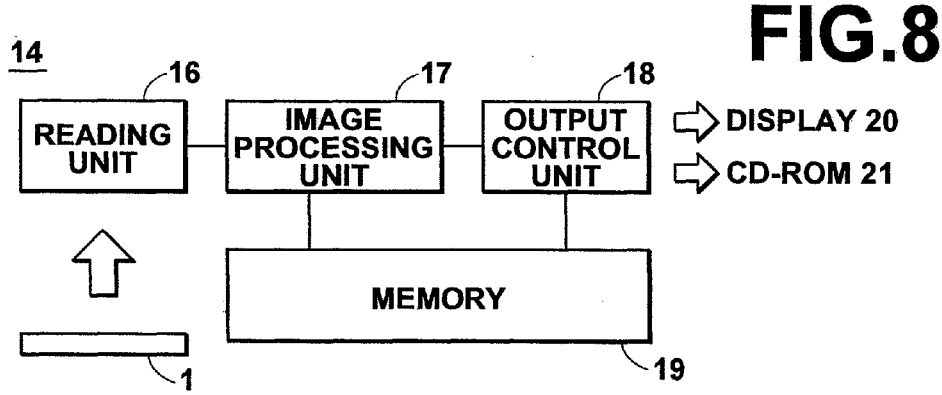
FIG. 8 is a block diagram of a print taking apparatus of the present invention that employs the recording medium shown in FIG. 1.

Referring now to FIG. 8, there is shown a print taking apparatus in accordance with the present invention. As shown in the figure, the print taking apparatus is equipped with the aforementioned recording medium 1 (or recording medium 8), a reading unit 16, an image processing unit 17, an output control unit 18, and memory 19. The reading unit 16 is used to receive light reflected from the recording medium 1, convert the reflected light into an electric signal, and generate image data. The image processing unit 17 is used to perform a predetermined image process on the image data generated by the reading unit 16. The memory 19 is used to store the image data processed by the image processing unit 17. The output control unit 18 is used to output to a display 20 the image data processed by the image processing unit 17 or image data stored in the memory 19, and to store these image data in an information recording medium, such as a CD-ROM.

The reading unit 16 can employ, for example, a CCD camera. The image processing unit 17, output control unit 18, and memory 19 can be realized by installing a control program for the CCD camera and an image processing program into a general-purpose personal computer.

When taking a print by the print taking apparatus 14, a print is first taken by impressing a human hand on the recording medium 1. Then, a digital image representing a substance adhering to the recording medium 1 is generated by the reading unit 16 and image processing unit 17. The generated digital image is temporarily stored in the memory 19. That is, the reading unit 16, image processing unit 17, and memory 19 function as image generation means.

The digital image stored on the memory 19 can be displayed on the screen of the display 20 by the output control unit 18. If there is a defect in the generated image by viewing the screen, the secretion adhering to the recording medium 1 is removed and a print is retaken. If an appropriate image is obtained, the output control unit 18 stores the digital image read out from the memory 19, on a portable recording medium such as a CD-ROM 21 or a hard disk (not shown). Thus, the output control unit 18 functions as data storage means.

Since the print taking apparatus of the present invention is constructed as described above, a print taken on the recording medium can be stored and utilized as a digital image. In addition, a print can be retaken any number of times until a digital image of a desired picture quality is obtained, so a high-quality print can be always taken.

While the present invention has been described with reference to the preferred embodiments thereof, the invention is not to be limited to the details given herein, but may be modified within the scope of the invention hereinafter claimed.

What is claimed is:

1. A set for obtaining prints of a part of the human body, comprising:
   a sheet member;
   a recording medium in which a plurality of metallic grains with an outside size of 200 nm or less are distributed over a surface layer, the recording medium being stuck on the sheet member;
   a recordable blank region disposed on the sheet member; and
   a transparent plastic film, comprising a material that has a refractive index different from any refractive index of secretions from human skin, wherein:
   an end of the transparent plastic film is stuck on the sheet member in advance of taking a print, and
   the transparent plastic film except the end is stuck on the surface layer of the recording medium after a print is taken, whereby secretions on the recording medium are covered with the transparent plastic film.

2. A set as defined by claim 1, wherein said transparent plastic film is a transparent film of polyethylene terephthalate or a transparent film of polycarbonate.

3. A set as defined by claim 1, wherein the transparent plastic film is movable to provide positioning prior to taking the print and after taking the print.

* * * * *